(12) United States Patent
Kimura et al.

(10) Patent No.: US 8,642,805 B2
(45) Date of Patent: Feb. 4, 2014

(54) METHOD OF PRODUCING PHTHALOYL DICHLORIDE COMPOUND, CATALYST FOR USE IN THE METHOD, AND METHOD OF FORMING THE CATALYST

(75) Inventors: Yoshikazu Kimura, Shizuoka (JP); Yoshihiro Takao, Shizuoka (JP); Toshimitsu Sugiyama, Shizuoka (JP); Takeshi Hanawa, Shizuoka (JP); Hiromichi Ito, Shizuoka (JP)

(73) Assignees: Iharanikkei Chemical Industry Co., Ltd., Shizuoka (JP); Nippon Light Metal Company, Ltd., Tokyo (JP)

( * ) Notice: Subject to any disclaimer, the term of this patent is extended or adjusted under 35 U.S.C. 154(b) by 282 days.

(21) Appl. No.: 13/056,483

(22) PCT Filed: Jul. 27, 2009

(86) PCT No.: PCT/JP2009/063362
§ 371 (c)(1),
(2), (4) Date: Jan. 28, 2011

(87) PCT Pub. No.: WO2010/013684
PCT Pub. Date: Feb. 4, 2010

(65) Prior Publication Data
US 2011/0178336 A1    Jul. 21, 2011

(30) Foreign Application Priority Data

Jul. 29, 2008  (JP) ................... 2008-194992
Oct. 28, 2008  (JP) ................... 2008-277165

(51) Int. Cl.
   *C07C 63/22*    (2006.01)
(52) U.S. Cl.
   USPC ......................................... 562/855; 562/861
(58) Field of Classification Search
   CPC ...................................... C07C 51/60
   See application file for complete search history.

(56) References Cited

U.S. PATENT DOCUMENTS

| | | | |
|---|---|---|---|
| 1,963,748 A | 6/1934 | Kyrides | |
| 1,963,749 A | 6/1934 | Kyrides | |
| 3,557,165 A | 1/1971 | Dorfman et al. | |
| 3,691,217 A * | 9/1972 | McCann | 562/861 |
| 4,165,337 A * | 8/1979 | Yoshinaka et al. | 562/855 |
| 4,785,111 A | 11/1988 | Toda | |
| 2005/0277788 A1 | 12/2005 | Job | |
| 2007/0299282 A1 | 12/2007 | Rohde et al. | |
| 2008/0039663 A1 | 2/2008 | Stolting et al. | |

FOREIGN PATENT DOCUMENTS

| | | | |
|---|---|---|---|
| JP | 47-27949 A | 10/1972 | |
| JP | 61-155350 A | 7/1986 | |
| JP | 62-123161 A | 6/1987 | |
| JP | 4-117344 A | 4/1992 | |
| JP | 7-53418 A | 2/1995 | |
| JP | 2004-167376 A | 6/2004 | |
| JP | 2005-330283 A | 12/2005 | |
| JP | 2008-505096 A | 2/2008 | |

(Continued)

OTHER PUBLICATIONS

White et al, Basic Energy Sciences Advisory Committee Subpanel Workshop Report, Opportunities for Catalysis in the 21st Century, 2002, pp. 1-47.*

(Continued)

*Primary Examiner* — Paul A Zucker
(74) *Attorney, Agent, or Firm* — Birch, Stewart, Kolasch & Birch, LLP

(57) ABSTRACT

A method of producing a phthaloyl dichloride compound, the method including: providing a compound represented by the following formula (1) and a compound represented by the following formula (2); and bringing the compound represented by the following formula (1) and the compound represented by the following formula (2) into reaction, so as to form a compound represented by the following formula (3), in the presence of at least one compound selected from a zirconium compound, a hafnium compound, and zinc oxide;

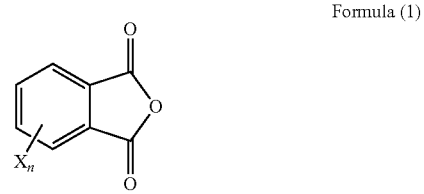

Formula (1)

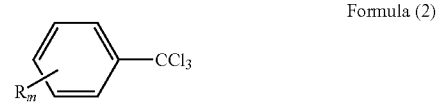

Formula (2)

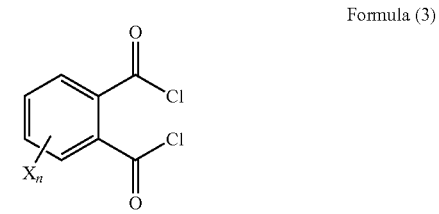

Formula (3)

wherein, in formulae, X represents a hydrogen atom, a halogen atom, a nitro group, a methyl group, or a methoxy group; when the X is plural, Xs may be the same or different from each other; n represents an integer of from 0 to 2; R represents a halogen atom, a chlorocarbonyl group, a low carbon number alkyl group, or a halogen-substituted low carbon number alkyl group; when the R is plural, Rs may be the same or different from each other; and m represents an integer of from 0 to 2.

4 Claims, No Drawings

(56) References Cited

FOREIGN PATENT DOCUMENTS

| JP | 2008-521845 A | 6/2008 |
|---|---|---|
| WO | WO 2006/004822 A1 | 1/2006 |
| WO | WO 2006/056436 A1 | 6/2006 |
| WO | WO 2006/058642 A1 | 6/2006 |

OTHER PUBLICATIONS

International Search Report for PCT/JP2009/063362, mailed Oct. 13, 2009.

Kyrides, "Phthayl Chloride," Journal of the American Chemical Society, 1937, 59 (1), p. 206-208.

Ott, "Symmetical and Unsymmetrical o-Phthalyl Chlorides," Organic Synthese, 1943, Coll. vol. 2, p. 528-530.

Davies, W. et al, "Action of some metallic oxides on benzotrichloride and benzal chloride," Journal of the Chemical Society, 1932, vol. part II, pp. 2808-2809.

Extended European Search Report for Appl. No. 09802927.5 dated Aug. 19, 2013.

Izmer, V.V. et al, "Synthesis and molecular structures of zirconium and hafnium complexes bearing dimethylsilandiyl-bis-2,4,6-trimethylindenyl and dimethylsilandiyl-bis-2-methyl-4,6-diisopropylindenyl ligands," Journal of Organometallic Chemistry, 2005, vol. 690, No. 4, pp. 1067-1079.

Japanese Office Action for Appl. No. 2008-277165 dated Sep. 3, 2013 (w/ English language translation).

Japanese Office Action for Appl. No. 2009-175884 dated Dec. 17, 2013 (w/ English translation).

\* cited by examiner

METHOD OF PRODUCING PHTHALOYL DICHLORIDE COMPOUND, CATALYST FOR USE IN THE METHOD, AND METHOD OF FORMING THE CATALYST

CROSS REFERENCE TO RELATED APPLICATIONS

This application claims priority on Patent Application No. 2008-277165 filed in Japan on Oct. 28, 2008 and Patent Application No. 2008-194992 filed in Japan on Jul. 29, 2008, respectively, which are entirely herein incorporated by reference.

TECHNICAL FIELD

The present invention relates to a method of producing a high-purity phthaloyl dichloride compound that may be useful for agrochemical raw materials, pharmaceutical raw materials, polymer raw materials, resin additives, insecticide raw materials, or the like, a catalyst for use in the method, and a method of forming the catalyst.

BACKGROUND ART

There are known methods of producing a phthalic dichloride compound; a method of chlorinating ortho-xylene and then hydrolyzing the resultant, and a method of bringing a phthalic anhydride compound in reaction with a chlorinating agent.

Examples of the method of using ortho-xylene as a starting material include a method in which 1-dichloromethyl-2-(trichloromethyl)benzene is produced by photo-chlorination of ortho-xylene, and then hydrolyzed to produce 3-chlorophthalide, and then the produced 3-chlorophthalide is subjected to photo-chlorination (refer to Patent Literature 1). However, this method needs equipments for photo-chlorination and requires multistep-production processes using a massive amount of chlorine.

Meanwhile, examples of the method of using a phthalic anhydride compound as a starting material include the following method. For example, a method in which phthalic anhydride is reacted with phosphorous pentachloride is disclosed (refer to Non-Patent Literature 1). However, this method produces waste containing a massive amount of phosphorus.

Further, examples of the method include a method in which a phthalic anhydride compound is reacted with phosgene or thionyl chloride (refer to Patent Literatures 2 to 5). In the method, special production equipment is needed because toxic and dangerous phosgene is to be handled. Besides, in the case of using thionyl chloride, equipment is needed for reaction of thionyl chloride under high-pressure.

In addition, examples of the method include a method in which phthalic anhydride is reacted with (trichloromethyl) benzene in the presence of zinc chloride (refer to Non-Patent Literature 2 and Patent Literatures 6 and 7). This method is a convenient method in which the reaction is carried out in an ordinary reactor (oven). However, it is necessary to use a massive amount of zinc chloride depending on a reaction temperature. According to the Non-Patent Literature 2, for example, it is reported that when zinc chloride is used in an amount of 10 mole % with respect to phthalic anhydride, the reaction proceeds at a temperature of from 110° C. to 120° C. Such a great amount of catalyst is however not practical. In contrast, if the amount of zinc chloride is reduced to 1 mole % which is still a large quantity, such high temperature as 200° C. is needed to achieve a practical reaction speed. It is difficult for an ordinary aqueous medium to act as a heating medium for realizing such high reaction temperature. On instead, a special medium is needed. Further, special equipments for addressing this demand must be provided.

Patent Literature 1: JP-A-47-27949 public patent bulletin
Patent Literature 2: International Publication (WO) No. 2006/056436 pamphlet
Patent Literature 3: JP-A-2005-330283 public patent bulletin
Patent Literature 4: US Patent Application Publication No. 2007/299282 specification
Patent Literature 5: International Publication (WO) No. 2006/058642 pamphlet
Patent Literature 6: U.S. Pat. No. 1,963,748 specification
Patent Literature 7: U.S. Pat. No. 1,963,749 specification
Non-Patent Literature 1: Org. Synth. Coll. Vol II, page 528
Non-Patent Literature 2: J. Am. Chem. Soc., Vol. 59, page 206 (1937)

DISCLOSURE OF INVENTION

Problem to be Solved by the Invention

With respect to the purity of a target compound in the product, an unreacted raw material (phthalic anhydride compound) remains in the methods described in Patent Literatures 2, 4 to 7, and Non-Patent Literatures 1 and 2 (any specific purity is not disclosed in Patent Literature 1). As a result, the purity of the phthaloyl dichloride compound remains at highest in the range of from 95% to 97%. In Example 4 of Patent Literature 3, a case example in which phthaloyl dichloride with a purity of 99% or more has been produced is described. However, this method needs to use phosgene that is difficult to handle as mentioned above. Moreover, the method needs to use an expensive N,N-dicyclohexylformamide as a catalyst. This method, even though purity is increased thereby, is unsuitable for industrial production in which efficiency and economy are demanded.

In a case in which a purity of a target compound is not increased and phthalic anhydride and phthaloyl dichloride are mixed in the product, these compounds need to be separated from each other by distillation or recrystallization. In fact, they are separated by these methods in Non-Patent Literature 1. However, separation is very difficult because their boiling points and melting points are close. Ordinarily, even though distillation is carried out after reaction, appreciable amounts of phthalic anhydride remain. The reaction in which phthaloyl dichloride is obtained from the above-described phthalic anhydride is an equilibrium reaction. Accordingly, even though a reaction speed is increased by using a catalyst, ordinarily the equilibrium state does not change. As a result, it is not easy to increase the purity of phthaloyl dichloride that is aimed.

The phthaloyl dichloride compound produced by the method in the above-described Patent Literatures 6 and 7 is nothing more than a compound with a purity of at highest about 95%, unless the compound is subjected to a special refining treatment. As a result, about 5% of unreacted phthalic anhydride is mixed therein. The reason is as follows. In the methods described in the above-described Patent Literatures, it is difficult for the purity of phthalic anhydride to increase more than 95%. As a result, about 5% of phthalic anhydride that has been used as a raw material remains. On account that the boiling point of phthalic anhydride and phthaloyl dichloride is very close each other and moreover phthalic anhydride has a sublimation property, it is very difficult to completely separate one from the other even in the case of using a multistep distillation equipment that is ordinarily used in an industrial production.

Further, the above-described Patent Literature 2 describes that when zinc chloride is used in an amount of 10% by mass with respect to phthalic anhydride and the reaction is carried out at a temperature of from 110° C. to 120° C., phthaloyl dichloride with a purity of 95% is obtained. That means about 5% of phthalic anhydride is still mixed as an impurity. Patent Literatures 6 and 7 describe that when a reaction is carried out using 1% by mass of zinc chloride at 200° C. for 20 hours, phthaloyl dichloride with a yield of 95% can be produced. However, there is no description about purity of the target product. Meanwhile, these literatures describe that zinc oxide may be used instead of (may substitute) zinc chloride, and presume that zinc oxide may probably react to produce zinc chloride. Further, these literatures describe that zinc powder may be similarly used. However, the results to show a fact that these assumptions were substantiated are not described therein. Further, information about yield and purity of the obtained product is not revealed.

That is, an unreacted phthalic anhydride inevitably remains in a proportion of about 5% in known methods. As described above, because of physical properties, it is very difficult for the unreacted phthalic anhydride to be eliminated by means of ordinary distillation or recrystallization. As a result, impurities that are unnecessary to phthaloyl dichloride at the time of commercialization of product are mixed therein. In view of industrial use, if it is desired to produce a high-purity phthaloyl dichloride from phthalic anhydride with an actual efficiency, without using unrealistic refining treatments, the only way to achieve the desire is to improve the rate of reaction thereby decreasing remaining of phthalic anhydride as small as possible. However, a catalyst for achieving the above desire is not known yet.

In this way, it is substantially impossible to industrially produce a phthaloyl dichloride compound with a purity of, for example, 99% or more. Alternatively, such industrial production was attended with much difficulty, namely necessity of cumbersome and special treatment processes.

In view of the above situation, the present invention is to address a method for production of a phthaloyl dichloride compound, in which an industrially useful and high-purity phthaloyl dichloride compound can be obtained by materials and a process flow that are economical and excellent in safety and handling, without any cumbersome treatment processes and, if necessary, with high yield and ultrahigh purity of 99% or more, and a catalyst for use in the method, and a method for preparation of the catalyst.

Means for Solving Problem

As a result of intensive investigation for addressing the above subject, the present inventors have found that a high-purity phthaloyl dichloride compound can be obtained by bringing a phthalic anhydride compound and a (trichloromethyl)benzene compound into reaction in the presence of a catalyst including a zirconium compound, a hafnium compound, or zinc oxide. On the basis of this finding, the present invention of the following composition has been completed.

That is, the present invention is as follows:
(1) A method of producing a phthaloyl dichloride compound, the method comprising:
providing a compound represented by the following formula (1) and a compound represented by the following formula (2); and
bringing the compound represented by the following formula (1) and the compound represented by the following formula (2) into reaction, so as to form a compound represented by the following formula (3), in the presence of at least one compound selected from a zirconium compound, a hafnium compound, and zinc oxide;

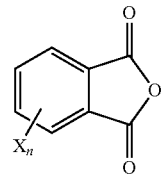

Formula (1)

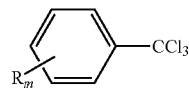

Formula (2)

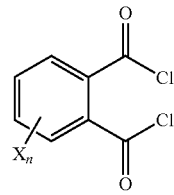

Formula (3)

wherein, in formulae, X represents a hydrogen atom, a halogen atom, a nitro group, a methyl group, or a methoxy group; when the X is plural, Xs may be the same or different from each other; n represents an integer of from 0 to 2; R represents a halogen atom, a chlorocarbonyl group, a low carbon number alkyl group, or a halogen-substituted low carbon number alkyl group; when the R is plural, Rs may be the same or different from each other; and m represents an integer of from 0 to 2.

(2) A method of producing a phthaloyl dichloride compound, the method comprising:
providing a compound represented by the following formula (1-1) and a compound represented by the following formula (1-2); and
bringing the compound represented by the following formula (1-1) and the compound represented by the following formula (1-2) into reaction, so as to form a compound represented by the following formula (1-3), in the presence of a zirconium compound and/or a hafnium compound;

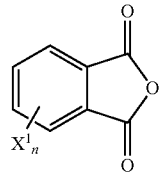

Formula (1-1)

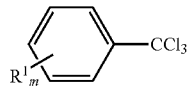

Formula (1-2)

-continued

Formula (1-3)

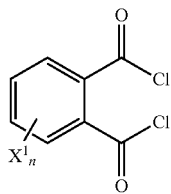

wherein, in formulae, $X^1$ represents a halogen atom, a nitro group, a methyl group, or a methoxy group; when the $X^1$ is plural, $X^1$s may be the same or different from each other; n represents an integer of from 0 to 2, $R^1$ represents a halogen atom, a chlorocarbonyl group, a low carbon number alkyl group, or a halogen-substituted low carbon number alkyl group; when the $R^1$ is plural, $R^1$s may be the same or different from each other; and m represents an integer of from 0 to 2.

(3) The method of producing a phthaloyl dichloride compound according to (2), wherein the zirconium compound and/or the hafnium compound are zirconium chloride and/or hafnium chloride.

(4) The method of producing a phthaloyl dichloride compound according to (2) or (3), wherein the compound represented by the formula (1-1) is phthalic anhydride.

(5) The method of producing a phthaloyl dichloride compound according to (2) or (3), wherein the compound represented by the formula (1-1) is 3-chlorophthalic anhydride or 4-chlorophthalic anhydride.

(6) The method of producing a phthaloyl dichloride compound according to any one of (2) to (5), wherein the compound represented by the formula (1-2) is 1-chloro-4-(trichloromethyl)benzene.

(7) A catalyst for use in a method of producing a phthaloyl dichloride compound, the catalyst comprising a zirconium compound and/or a hafnium compound; and the catalyst being used in the reaction between a compound represented by the following formula (1-1) and a compound represented by the following formula (1-2), so as to form a compound represented by the following formula (1-3);

Formula (1-1)

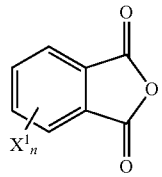

Formula (1-2)

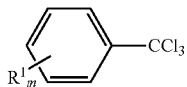

Formula (1-3)

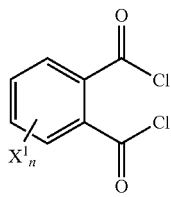

wherein, in formulae, $X^1$ represents a halogen atom, a nitro group, a methyl group, or a methoxy group; when the $X^1$ is plural, $X^1$s may be the same or different from each other; n represents an integer of from 0 to 2; $R^1$ represents a halogen atom, a chlorocarbonyl group, a low carbon number alkyl group, or a halogen-substituted low carbon number alkyl group; when the $R^1$ is plural, $R^1$s may be the same or different from each other; and m represents an integer of from 0 to 2.

(8) A method of producing a phthaloyl dichloride compound, the method comprising:

providing a compound represented by following formula (2-1) and a compound represented by the following formula (2-2); and bringing the compound represented by the following formula (2-1) and the compound represented by the following formula (2-2) into reaction, so as to form a compound represented by the following formula (2-3), using zinc oxide as a catalyst;

Formula (2-1)

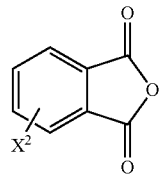

Formula (2-2)

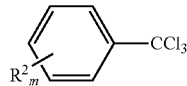

Formula (2-3)

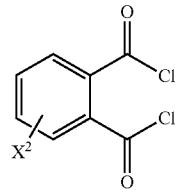

wherein, in formulae, $X^2$ represents a hydrogen atom or a halogen atom; $R^2$ stands for any one of a halogen atom, a low carbon number alkyl group and a halogen-substituted low carbon number alkyl group; when the $R^2$ is plural, $R^2$s may be the same or different from each other; and m represents an integer of from 0 to 2.

(9) The method of producing a phthaloyl dichloride compound according to (8), wherein the compound represented by the formula (2-1) is phthalic anhydride.

(10) The method of producing a phthaloyl dichloride compound according to (8), wherein the compound represented by the formula (2-1) is 3-chlorophthalic anhydride or 4-chlorophthalic anhydride.

(11) The method of producing a phthaloyl dichloride compound according to any one of (8) to (10), wherein the compound represented by the formula (2-2) is 1-chloro-4-(trichloromethyl)benzene.

(12) The method of producing a phthaloyl dichloride compound according to any one of (8) to (10), wherein the compound represented by the formula (2-2) is (trichloromethyl)benzene.

(13) A method of forming a zinc chloride catalyst for use in a method of producing a phthaloyl dichloride compound, the method comprising:

providing zinc oxide and a (trichloromethyl)benzene compound represented by the following formula (2-2); and bringing the zinc oxide and the (trichloromethyl)benzene compound into reaction;

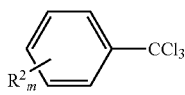

Formula (2-2)

wherein, in formula, $R^2$ stands for any one of a halogen atom, a low carbon number alkyl group and a halogen-substituted low carbon number alkyl group; when the $R^2$ is plural, $R^2$s may be the same or different from each other; and m represents an integer of from 0 to 2.

(14) A method of producing a phthaloyl dichloride compound, the method comprising:

preparing a zinc chloride catalyst according to the method of (13); and bringing a phthalic anhydride compound represented by the following formula (2-1) and a (trichloromethyl)benzene compound represented by the above-described formula (2-2) into in-situ reaction, so as to form a phthaloyl dichloride compound represented by following formula (2-3), using the zinc chloride catalyst within the same environment as preparation of the zinc chloride catalyst;

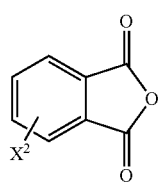

Formula (2-1)

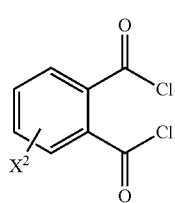

Formula (2-3)

wherein, in formulae, $X^2$ represents a hydrogen atom or a halogen atom.

(15) A zinc chloride catalyst prepared according to the method of (13), wherein the zinc chloride catalyst is used in a method of producing a phthaloyl dichloride compound, the method comprising:

bringing a phthalic anhydride compound represented by the following formula (2-1) and a (trichloromethyl)benzene compound represented by the above-described formula (2-2) into in-situ reaction, so as to form a phthaloyl dichloride compound represented by the following formula (2-3) within the same environment as preparation of the zinc chloride catalyst;

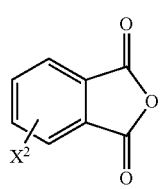

Formula (2-1)

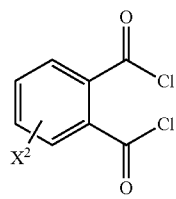

Formula (2-3)

wherein, in formulae, $X^2$ represents a hydrogen atom, or a halogen atom.

Effect of Invention

According to the production method and the catalyst involved in a first aspect of the present invention, it is possible to obtain an industrially useful and high-purity phthaloyl dichloride compound, that is required as a raw material of pharmaceutical chemicals, agrochemicals, and various kinds of polymer compounds. Further, the method and catalyst enable a convenient method of using materials that are superior in handling without leading toxicity and risk, and further without causing a cumbersome refining process while with a high yield. Moreover, according to the production method and the catalyst involved in the first aspect, it is possible to produce a high-purity phthaloyl dichloride compound that has been difficult to obtain in the past, by a method of using a small amount of a catalyst at a mild reaction temperature without a special heat medium. The production method can thereby be preferably used for a mass production of industrial scale.

According to the production method involved in a second aspect of the present invention, it is possible to obtain an industrially useful and high-purity phthaloyl dichloride compound with safety, efficiency and a high yield, while without a cumbersome process flow and a special treatment. Further, the zinc chloride catalyst according to the inventive aspect can be prepared at low cost, and zinc oxide that corresponds to a raw material of zinc chloride is also easy to handle in an industrial scale. Accordingly, the zinc chloride catalyst is especially suitable as a catalyst for the production of phthaloyl dichloride compound. Further, the production method according to the aspect exhibits such a remarkable effect that the phthaloyl dichloride compound produced by the method can be obtained as an ultrahigh-purity product, if necessary with a purity of 99% or more, even without a processing such as an elimination treatment of unnecessary impurities. The phthaloyl dichloride compound obtained by the inventive production method is thus extremely useful as a raw compound for insecticides or the like in which especially high purity is required.

Other and further features and advantages of the invention will appear more fully from the following description.

BEST MODE FOR CARRYING OUT THE INVENTION

The production method of the present invention, bringing the above-described formula (1) and the compound represented by the above-described formula (2) into reaction, so as to form a compound represented by the above-described formula (3), in the presence of at least one compound selected from a zirconium compound, a hafnium compound, and zinc oxide. The present invention is preferably a first embodiment or a second embodiment as described below. The inventions involved in these embodiments have the same or corresponding technical features, and constitute a group of inventions as the above-described invention. Hereinafter, the first embodiment and the second embodiment are explained in detail with respect to each embodiment, even though some common description emerges. However, the present invention should not be construed as being limited to these embodiments.

<First Embodiment>

In the production method of the phthaloyl dichloride compound according to the present embodiment, the phthalic anhydride compound represented by the above-described formula (1-1) and the (trichloromethyl)benzene compound represented by the above-described formula (1-2) are brought into reaction in the presence of a zirconium compound and/or a hafnium compound as a catalyst.

In the compound represented by the above-described formula (1-1), a substitution position of the substituent $X^1$ on the benzene ring is not limited. However, when a sterically-hindered substituent is located at ortho-position, it is preferable to increase an amount of the catalyst or to elevate a reaction temperature. Specific examples of the compound represented by the above-described formula (1-1) include phthalic anhydride, 3-chlorophthalic anhydride, 4-chlorophthalic anhydride, 4,5-dichlorophthalic anhydride, 3,6-chlorophthalic anhydride, 3-nitrophthalic anhydride, 4-nitrophthalic anhydride, 3-methoxyphthalic anhydride, and 4-methylphthalic anhydride.

n as a number of the substituent $X^1$ is in the range of from 0 to 2. However, n is preferably 0 or 1.

In the compound represented by the above-described formula (1-2), the substituent $R^1$ is not particularly limited. However, it is preferable that $R^1$ is not a substituent having a hydroxyl group that is easy to be chlorinated, for example —COOH, —COSH, —OH, or the like. A substitution position of the substituent $R^1$ is not particularly limited.

Examples of the substituent $R^1$ include halogen atoms such as chlorine, or bromine; a chlorocarbony group; a low carbon number alkyl group such as a methyl group or an ethyl group; and a halogen-substituted low carbon number alkyl group such as a trichloromethyl group, a dichloromethyl group, or a chloromethyl group. The low carbon number alkyl group is preferably an alkyl group having 1 to 3 carbon atoms.

Specific examples of the compound represented by the formula (1-2) include 1-chloro-4-(trichloromethyl)benzene, 1-chloro-2-(trichloromethyl)benzene, 2,4-dichloro-1-(trichloromethyl)benzene, 3,4-dichloro-1-(trichloromethyl)benzene, 1-methyl-4-(trichloromethyl)benzene, 1,4-bis(trichloromethyl)benzene, and 1,3-bis(trichloromethyl)benzene. Further, unsubstituted (trichloromethyl)benzene is inexpensive, and also preferably used from a viewpoint of economical advantages.

An amount of the compound represented by the formula (1-2) is preferably in the range of from 1.0 to 3.0 equivalent amounts, and more preferably from 1.3 to 1.8 equivalent amounts, in terms of a trichloromethyl group contained in the compound, with respect to the compound represented by the formula (1-1) to be reacted with the compound represented by the formula (1-2).

In the production method of the phthaloyl dichloride compound according to the present embodiment, a catalyst including a zirconium compound and/or a hafnium compound is used. Examples of the catalyst composed of a zirconium compound include zirconium tetrachloride, zirconium oxide, dichlorooxo zirconium (zirconium oxychloride), zirconium hydroxide, tetrabutoxy zirconium, tetraisopropoxy zirconium, zirconium carbonate, zirconium carbide, and metal zirconium. Examples of the catalyst composed of a hafnium compound include hafnium tetrachloride, hafnium oxide, hafnium carbonate, hafnium oxychloride, hafnium hydroxide, and metal hafnium. Among them, zirconium tetrachloride and/or hafnium tetrachloride are preferable. With respect to a zirconium compound and a hafnium compound, it is enough in the present invention to incorporate at least one of a zirconium compound or a hafnium compound. For example, in a case in which separation is inevitably difficult, mixing of these compounds may be acceptable. Further, compounds other than these compounds may be further contained at the level by which the effect of the present invention is not deteriorated.

The reaction between a phthalic anhydride compound and a (trichloromethyl)benzene compound to produce phthaloyl dichloride is an equilibrium reaction. If the reaction reaches an equilibrium state, even though a reaction time is extended, a remaining raw material is not reduced any more. As a result, a reaction yield or purity of the target product is not increased. In contrast, in the production method of the phthaloyl dichloride compound according to the present embodiment, as the mechanism of action of the catalyst is not yet clear, the purity of the objective product can be increased as mentioned above by using the above-described catalyst even though a target reaction is an equilibrium reaction.

A usage amount of the above-described catalyst including a zirconium compound and/or a hafnium compound is preferably in the range of from 0.05% by mole to 10% by mole, and more preferably from 0.1% by mole to 1.0% by mole, with respect to the compound represented by the above-described formula (1-1). This range can be preferably fitted in the industry application. Further, this range has an advantage in that a reaction can be completed in a short time with a high yield.

In the production method of the phthaloyl dichloride compound according to the present embodiment, a reaction temperature at which the compound represented by the above-described formula (1-1) and the compound represented by the above-described formula (1-2) are brought into reaction is in the range of preferably from 120° C. to 200° C. and more preferably from 140° C. to 160° C. This reaction time varies according to the conditions such as a reaction scale and a reaction temperature. The reaction can be completed in the period of preferably from 3 hrs to 20 hrs and more preferably 5 hrs to 8 hrs. Further, the above-described range of reaction temperature has an advantage in that an aqueous medium useful for the industrial production can be used as a heat medium by setting the reaction temperature to such range of reaction temperature. In the present embodiment, the above-described reaction is preferably carried out in the absence of solvent.

In the production method of the phthaloyl dichloride compound according to the present embodiment, a target compound represented by the above-described formula (1-3) can be obtained with a high purity. For example, the target compound can be obtained with a high purity of 98% or more without an additional refining process. Further, if necessary, the purity can be increased to the level of from 99.0% to 99.5% by controlling a reaction condition or the like. Even in a use application in which a required purity is so extremely high that a compound with a purity of from 95% to 97% that is obtained by a conventional method is difficult to use, a target compound obtained by the production method of the present embodiment can be directly applied without any further modification. Accordingly, the production method of the present embodiment has an advantage in that it is not necessary to use a cumbersome refining process for eliminating a material that is difficult to separate, for example, an unreacted phthalic anhydride compound. In the present embodiment, unless otherwise indicated, the purity refers to a purity of a target product after byproducts have been eliminated by an ordinary rectification, and when represented simply by "%", the "%" means % by mole.

In the production method of the phthaloyl dichloride compound according to the present embodiment, an unreacted compound represented by the formula (1-2), a compound in which a trichloromethyl group has been changed to a chlorocarbonyl group after reaction of the compound represented by the formula (1-2), and a catalyst including a zirconium compound and/or a hafnium compound, each of which may be mixed in a system after completion of reaction, are easy to be separated. Accordingly, these compounds may be easily separated from the target compound represented by the formula (1-3) by an ordinary distillation operation, or the like. A remained amount of an unreacted compound represented by the formula (1-1) is usually a minute amount. The unreacted compound may be used as it is, without refining. If necessary, separation may be performed by a distillation operation or the like whereby a purity of the target compound may be further increased.

<Second Embodiment>

In the production method of the phthaloyl dichloride compound according to the present embodiment, the phthalic anhydride compound represented by the above-described formula (2-1) and the (trichloromethyl)benzene compound represented by the above-described formula (2-2) are brought into reaction to produce the phthaloyl dichloride compound represented by the above-described formula (2-3) using zinc oxide as a catalyst.

In the formulae (2-1) and (2-3), $X^2$ represents a hydrogen atom or a halogen atom. Among them, a hydrogen atom or a chlorine atom is preferable. A substitution position of the substituent $X^2$ on the benzene ring is not limited. However, when a sterically-hindered substituent is located at ortho-position, it is preferable that an amount of the catalyst is increased, or a reaction temperature is elevated. Specific examples of the compound represented by the above-described formula (2-1) include phthalic anhydride, 3-chlorophthalic anhydride, or 4-chlorophthalic anhydride.

In the above-described formula (2-2), the above described substituent $R^2$ stands for a halogen atom, a low carbon number alkyl group and a halogen-substituted low carbon number alkyl group. Examples of the substituent $R^2$ include halogen atoms such as chlorine, or bromine; a chlorocarbony group; a low carbon number alkyl group such as a methyl group or an ethyl group; and a halogen-substituted low carbon number alkyl group such as a trichloromethyl group, a dichloromethyl group, or a chloromethyl group. The low carbon number alkyl group is preferably a low carbon number alkyl group having 1 to 3 carbon atoms. The halogen atom is preferably a chlorine atom.

Specific examples of the compound represented by the above-described formula (2-2) include (trichloromethyl)benzene, 1-chloro-4-(trichloromethyl)benzene, 1-chloro-2-(trichloromethyl)benzene, 2,4-dichloro-1-(trichloromethyl)benzene, 3,4-dichloro-1-(trichloromethyl)benzene, 1,4-bis(trichloromethyl)benzene, and 1,3-bis(trichloromethyl)benzene. Among them, the compound represented by the formula (2-2) is preferably 1-chloro-4-(trichloromethyl)benzene or (trichloromethyl)benzene.

An amount of the compound represented by the above-described formula (2-2) is preferably in the range of from 1.0 to 3.0 equivalent amounts, and more preferably from 1.3 to 1.8 equivalent amounts, in conversion of a trichloromethyl group contained in the compound, with respect to the compound represented by the formula (2-1).

The kind of zinc oxide used in the present embodiment is not limited. However, well-dried zinc oxide is preferably used. The usage amount of zinc oxide is in the range of preferably from 0.05% by mole to 10% by mole, and more preferably from 0.5% by mole to 1.0% by mole, with respect to the compound represented by the above-described formula (2-1). By using the above-described catalyst in this range, it is possible to complete a desirable reaction with a furthermore good yield in a short time. In the production method of the present embodiment, compounds or the like other than the above-described compounds are not obstructed to be added to a reaction system. Further, the above-described zirconium compound and/or hafnium compound may be contained in zinc oxide used as a catalyst. Further, other materials may be added at a level by which an effect of the present invention is not deteriorated.

In the production method of the present embodiment, it is preferable to use zinc oxide, or a zinc chloride catalyst that is obtained by bringing zinc oxide and a (trichloromethyl)benzene compound represented by the above-described formula (2-2) into reaction. In this time, it is preferable that a phthaloyl dichloride compound represented by following formula (2-3) is produced by bringing a phthalic anhydride compound represented by the above-described formula (2-1) and a (trichloromethyl)benzene compound represented by the above-described formula (2-2) into in-situ reaction in the system in which the above-described particular zinc chloride catalyst has been prepared. Alternatively, the phthaloyl dichloride compound may be produced by a method of at first, without adding a compound represented by the above-described formula (2-1), preparing a high-activity zinc chloride catalyst from zinc oxide and a compound represented by the above-described formula (2-2) in a reaction system, and thereafter adding the compound represented by the above-described formula (2-1) to the reaction system to bring them into reaction. Alternatively, it is possible to produce the phthaloyl dichloride compound while preparing a zinc chloride catalyst by bringing zinc oxide and a compound represented by the above-described formula (2-2) into reaction in the presence of a compound represented by the formula (2-1).

Herein, the following is an explanation of a special mechanism of action of zinc oxide and zinc chloride as a catalyst in the production method of phthaloyl dichloride according to the present embodiment, in which the explanation partially includes estimation.

Zinc chloride has a hygroscopic nature. For this nature, even though zinc chloride is stored so as to be maintained in the dry state, and then introduced to a reaction system, moisture absorption of zinc chloride is inevitable to some extent. As a result, catalyst activity of zinc chloride may be lowered. In contrast, zinc oxide is not high in terms of hygroscopic nature in air. Therefore, it is estimated that deterioration of catalyst as mentioned above may not occur, so that a high catalyst activity may be obtained. Especially, when zinc chloride is used in a massive amount to make the production suitable for industrial scale, it is difficult to maintain the dry state of zinc chloride. In this case, a stabilization effect of the catalytic action due to the above described use of zinc oxide becomes more conspicuous. Further, it is estimated that zinc oxide reacts with a compound represented by the above-described formula (2-2), and as a result of the reaction, a special catalytic surface that is different from the surface obtained by production of zinc chloride according to other methods has been formed, namely during reaction of forming phthaloyl dichloride, especially high-activity zinc chloride or its surface has been formed. It is estimated that, combined with suppressive action of catalyst deterioration due to moisture absorption, the highly-activated zinc chloride catalyst prepared from zinc oxide has made it possible to achieve the production of phthaloyl dichloride with extremely-high purity that could not be achieved in the past.

A temperature of the reaction between the compound represented by the above-described formula (2-1) and the compound represented by the formula (2-2) varies in accordance with a use amount of a catalyst. However, the temperature is in the range of preferably from 160° C. to 220° C. and more preferably from 180° C. to 200° C. A reaction time varies in accordance with the conditions such as a reaction scale and a reaction temperature. However, for example, the reaction can be completed within a period of from 8 hrs to 30 hrs. In the present embodiment, the above-described reaction is preferably carried out in the absence of solvent.

According to the production method of the present embodiment, phthaloyl dichloride can be obtained with a high purity. For example, phthaloyl dichloride with a purity of 99% or more at the state immediately after reaction can be obtained without any particular processing.

In the production method of the present embodiment, three components of an unreacted compound represented by the formula (2-2), a compound in which a trichloromethyl group has been changed to a chlorocarbonyl group after reaction of the compound represented by the formula (2-2) (this modified compound can be also used as a compound useful for industrial materials) and the compound represented by the formula (2-3) which is a target compound are ordinarily mixed in a system after completion of reaction. However, these components are easy to be separated. An unreacted compound represented by the formula (2-1) may remain, even though a remained amount thereof is a minute amount. For example, the compound represented by the formula (2-1) may remain in an amount of from 0.5% to 1%. In other words, it is possible to obtain the compound represented by the formula (2-3) which is a target compound with a purity of from 99.0% to 99.5%. This means that a target compound is obtained with much higher purity than the purity of from 93% to 97% that can be achieved in the case of producing the target compound by a practical technique that is known from the past.

According to the production method of the present embodiment, a high-purity phthaloyl dichloride compound may be obtained with a high yield by a convenient and safety method using a catalyst that is economical and easy to handle, but without any one of a risky catalyst, a promoter and the like. This advantage results in major contribution to the field of industrially producing insecticides or the like. For example, in a case in which phthaloyl dichloride is used as a raw material for producing a phthalamide compound that shows a high effect as an insecticide (refer to the reaction scheme A described below) and in the case of using a raw material in which a massive amount of phthalic anhydride is contained, a byproduct (reaction intermediate) [2] at the first stage results in remaining as an impurity (refer to the reaction scheme B described below) in the amidation reaction that is performed in two stages in the next step. This means reduction in performance of the insecticide together with reduction in yield. If desired to provide a high-quality product, impurity-eliminating operation is forced, even though the operation includes cumbersome steps. Alternatively, it is contemplated that carboxylic acid is activated using methyl chloroformate or the like in order to convert byproduct [2] to phthalamide [3]. However, this reaction does not proceed only by directly acting $R^{22}NH_2$.

[Reaction Scheme A]

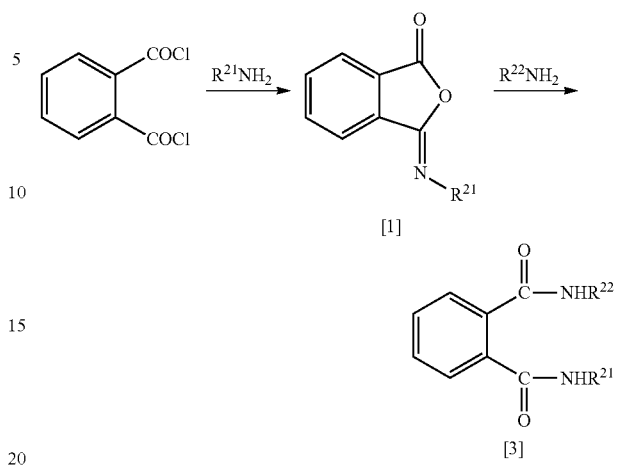

[Reaction Scheme B]

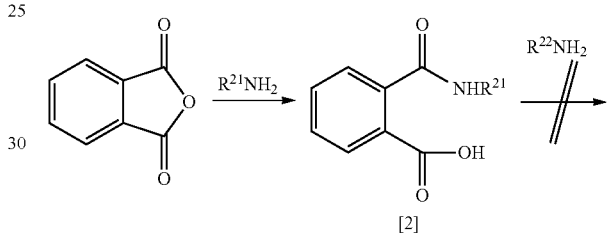

(In the above schemes, $R^{21}$ and $R^{22}$ represent an alkyl group or an aryl group)

In view of overcoming these difficulties, recently, a method of producing a phthalamide compound [3] via a reaction intermediate {1} has been developed (refer to JP-A-2002-326989). Further, research and development on improvement in performance of the insecticide including a phthalamide compound has been continued. Examples of the insecticide include high-performance insecticides described in European Patent Application Laid-open EP-A-1006107 and Fine Chemical (CMC Shuppan) Vol. 36, page 58 (2007). In order to provide a compound as a raw material suitable for these new techniques, a high-purity product in which phthaloyl dichlorid contains as few phthalic anhydride as possible is required. The production method of the present embodiment and the catalyst suitable for the production method make it possible to address such need.

EXAMPLE

Hereinafter, the present invention is explained in detail on the basis of Examples. However, the invention is not limited thereto. Further, hereinafter, "%" refers to "% by mole", unless otherwise indicated.

Examples Involved in First Embodiment

Example 1-1

In a 2L volume 4-necked flask, 444 g (3.0 moles) of phthalic anhydride, 690 g (3.0 moles) of 1-chloro-4-(trichloromethyl)benzene, and 0.9 g (3.8 mmoles, 0.13% with respect to phthalic anhydride) of anhydrous zirconium chloride were placed, and heated at 160° C. While keeping this temperature, 345 g (1.5 moles) 1-chloro-4-(trichloromethyl) benzene was added dropwise to the reaction mixture over 3 hours, and then stirring was still continued for 3 hours.

With respect to a liquid sample 1a that was already reacted, analysis was performed by gas chromatography (GC 2014 {trade name}, manufactured by Shimadzu Corporation, column: INERT CAP 5 {trade name}, manufactured by GL Sciences Inc., were used. The same goes for the following Examples and Comparative Examples). As a result, it was found that 0.82% of phthalic anhydride remained in the liquid sample 1a. The liquid sample 1a that was already reacted was distilled under reduced pressure, thereby obtaining 1456 g (yield: 98.6%) of colorless liquid 1b. A boiling point of the colorless liquid 1b was from 135° C. to 136° C./10 torr. The colorless liquid 1b was rectified by a 23-step distillation column, thereby obtaining sample 1 containing 425 g (yield of 70% on the basis of phthalic anhydride) of phthaloyl dichloride. A boiling point (bp) of sample 1 was from 120° C. to 122° C./4~5 torr (value of phthaloyl dichloride described in literature: by 131° C. to 133° C./9~10 mmHg: refer to Organic Synthesis Coll. VoIII, page 528). By the same analysis as the above gas chromatography, it was found that a purity of phthaloyl dichloride in the sample 1 was 99.0% and a residual rate of phthalic anhydride was 0.88%. Further, from the above-described liquid sample 1b, 487 g (yield of 93% on the basis of consumed 1-chloro-4-(trichloromethyl)benzene of 4-chlorobenzoyl chloride with a purity of 99.7% was obtained by distillation.

Example 1-2

A reaction was performed in the same manner as in Example 1-1, except that a 1 L volume flask was used and the amount of zirconium chloride in Example 1-1 was reduced from 0.13% to 0.065%. Namely, a mixture of 111 g (0.75 moles) of phthalic anhydride, 258 g (1.13 moles) of 1-chloro-4-(trichloromethyl)benzene, and 0.11 g (0.065% with respect to phthalic anhydride) of anhydrous zirconium chloride was stirred at 160° C. for 22 hours. A liquid sample 2a that was already reacted was distilled in the same manner as in Example 1-1, thereby obtaining sample 2. Gas chromatographic analysis of the sample 2 confirmed that 0.90% of phthalic anhydride remains and phthaloyl dichloride with a purity of 98.9% has been produced.

Example 1-3

A reaction was carried out in the same manner as in Example 1-2, except that the amount of anhydrous zirconium chloride was changed to 0.22 g (0.13% with respect to phthalic anhydride), and further the heating temperature (reaction temperature) of the mixture was set to 140° C. and the mixture was stirred for 27 hours. The liquid sample 3a that was already reacted was distilled in the same manner as in Example 1-1 to obtain sample 3. Gas chromatographic analysis of the sample 3 confirmed that 0.86% of phthalic anhydride remains and phthaloyl dichloride with a purity of 99.0% has been produced.

Example 1-4

A mixture of 253 g (1.71 moles) of phthalic anhydride, 503 g (2.57 moles) of (trichloromethyl)benzene and 0.50 g (0.13% with respect to phthalic anhydride) of anhydrous zirconium chloride was stirred at 160° C. for 19 hours. Gas chromatographic analysis of the liquid sample 4a that was already reacted confirmed that 1.95% of phthalic anhydride remains and phthaloyl dichloride with a yield of 95.5% has been produced. As a byproduct, a dimer of (trichloromethyl) benzene was formed with a yield of 1.9%. By rectification of this product, 208 g of phthaloyl dichloride was obtained with a purity of 98.0% (yield of 60% on the basis of phthalic anhydride).

Example 1-5

A mixture of 111 g (0.75 moles) of phthalic anhydride, 258 g (1.13 moles) of 1-chloro-4-(trichloromethyl)benzene and 0.22 g (0.09% with respect to phthalic anhydride) of anhydrous hafnium chloride was stirred at 160° C. for 13 hours. Sample 5a that was already reacted was distilled in the same manner as in Example 1-1 to obtain a sample 5. Gas chromatographic analysis of the sample 5 confirmed that 0.43% of phthalic anhydride remains and phthaloyl dichloride with a yield of 99.5% has been produced.

Example 1-6

In a 2L volume 4-necked flask, 365 g (2.0 mole) of 3-chlorophthalic anhydride, 460 g (2.0 moles) of 1-chloro-4-(trichloromethyl)benzene, and 1.83 g (0.39% with respect to 3-chlorophthalic anhydride) of anhydrous zirconium chloride were placed, and heated at 160° C. While keeping this temperature, 230 g (1.0 mole) of 1-chloro-4-(trichloromethyl)benzene was added dropwise to the reaction mixture over 3 hours, and then stirring was still continued for 13 hours. Gas chromatographic analysis of a liquid sample 6a that was already reacted confirmed that 0.65% of 3-chlorophthalic anhydride remains.

The liquid sample 6a that was already reacted was distilled under reduced pressure, thereby obtaining 992 g (yield: 94.6%) of colorless liquid 6b. A boiling point (bp) of the colorless liquid 6b was from 153° C. to 155° C./9 torr. The colorless liquid 6b was rectified by a 23-step distillation column, thereby obtaining sample 6 containing 290 g (yield of 61% on the basis of 3-chlorophthalic anhydride) of 3-chlorophthaloyl dichloride. A boiling point (b p) of sample 6 was from 134-138° C./4-5 torr (value in literature: b p 140° C./8 mbar: Patent Literature 5). As a result of gas chromatographic analysis, a purity of 3-chlorophthaloyl dichloride in the sample 6 was 99.0%. Further, 332 g (yield of 95% on the basis of consumed 1-chloro-4-(trichloromethyl)benzene of 4-chlorobenzoyl chloride with a purity of 99.7% was obtained by distillation.

Example 1-7

In a 200 mL volume 4-necked flask, 59.3 g (0.40 moles) of phthalic anhydride, 138.0 g (0.60 moles) of 1-chloro-4-(trichloromethyl)benzene, and 0.052 g (0.57 mmoles, 0.14% by mole with respect to phthalic anhydride) of metal zirconium (manufactured by Kanto Chemical Co., Inc., sponge-like) were placed, and stirring was continued at a temperature of from 155° C. to 156° C. for 18 hours. Gas chromatographic analysis of the reaction liquid confirmed that 0.97% of phthalic anhydride remains and 98.4% of phthaloyl dichloride has been produced.

Example 1-8

In a 300 mL volume 4-necked flask, 187.5 g (1.27 moles) of phthalic anhydride, 378.4 g (1.65 moles) of 1-chloro-4-

(trichloromethyl)benzene were placed, and heated up to 100° C. Thereafter, 1.30 g (4.0 mmoles, 0.32% with respect to phthalic anhydride) of zirconium oxychloride 8 hydrate was added and heated to 155° C. While keeping a temperature in the range of from 155° C. to 156° C., stirring was continued for 9 hours. GC analysis of the reaction liquid confirmed that 0.74% of phthalic anhydride remains and 98.4% of phthaloyl dichloride has been produced.

Example 1-9

In a 300 mL volume 4-necked flask, 93.8 g (0.63 moles) of phthalic anhydride, 218.3 g (0.95 moles) of 1-chloro-4-(trichloromethyl)benzene were placed, and heated up to 100° C. Thereafter, 0.32 g (2.0 mmole, 0.32% with respect to phthalic anhydride) of zirconium hydroxide was added and heated up to 160° C. At the same temperature, stirring was continued for 2 hours. Further, while keeping a temperature in the range of from 167° C. to 168° C., stirring was continued for 3 hours. GC analysis of the reaction liquid confirmed that 0.82% of phthalic anhydride remains and 98.6% of phthaloyl dichloride has been produced.

Example 1-10

In a 300 mL volume 4-necked flask, 93.8 g (0.63 moles) of phthalic anhydride, 218.3 g (0.95 moles) of 1-chloro-4-(trichloromethyl)benzene and 1.3 g (6.4 mmole, 1% by mole with respect to phthalic anhydride) of phthaloyl dichloride were placed, and heated up to 110° C. Thereafter, 0.32 g (2.0 mmoles, 0.32% with respect to phthalic anhydride) of zirconium hydroxide was added and heated up to 160° C. At the same temperature, stirring was continued for 4 hours. GC analysis of the reaction liquid confirmed that 0.96% of phthalic anhydride remains and 98.8% of phthaloyl dichloride (the added phthaloyl dichloride is excluded) has been produced.

Comparative Example 1-1

According to Non-Patent Literature 1, 14.8 g (0.10 moles) of phthalic anhydride and 22 g (0.106 moles) phosphorous pentachloride were brought into reaction at 150° C. for 16 hours. Gas chromatographic analysis of the sample 11a that was already reacted confirmed that phthaloyl dichloride with a yield of 88.8% has been produced and 6.8% of phthalic anhydride remains. By distilling the sample 11a as it is in the same manner as in Example 1-1, 18.2 g (yield of 89.7%) of phthaloyl dichloride fraction with a purity of 92.0% was obtained. It was found that 7.6% of phthalic anhydride came to be mixed in the fraction Comparative Example 1-2

A mixture of 222 g (1.50 moles) of phthalic anhydride, 517 g (2.25 moles) of 1-chloro-4-(trichloromethyl)benzene and 0.44 g (0.22% with respect to phthalic anhydride) of zinc chloride was stirred at 160° C. for 33 hours. The reacted mixture sample 22a was distilled in the same manner as in Example 1-1 thereby obtaining a sample 22. Gas chromatographic analysis of the sample 22 confirmed that 4.3% of phthalic anhydride remains and phthaloyl dichloride with a purity of 95.5% has been produced.

Examples Involved in Second Embodiment

Example 2-1

In a 2L volume 4-necked flask, 370 g (2.5 moles) of phthalic anhydride, 756 g (3.3 moles) of 1-chloro-4-(trichloromethyl), and 2.08 g (0.025 moles, 1% by mole with respect to phthalic anhydride) of zinc oxide were placed, and stirring was continued at 155° C. for 32 hours. By analysis of the reaction liquid using gas chromatography (GC) (GC 2014 {trade name}, manufactured by Shimadzu Corporation, column: INERT CAP 5 {trade name}, manufactured by GL Sciences Inc., The same GC apparatus and column are used in the Examples and Comparative Examples described below), it was found that 3.6% of phthalic anhydride remains. In view of this result, a reaction temperature was increased to 195° C. and stirring was still carried out for 9 hours. By the above-described GC analysis, it was found that a residual rate of phthalic anhydride was reduced to 0.48%. Accordingly, the reaction liquid was distilled under reduced pressure, and then rectified by a 20-step distillation column. As a result, 394 g of 4-chloro benzoyl chloride with a GC purity of 99.88% (yield of 90% on the basis of the reacted 1-chloro-4-(trichloromethyl)) and 326 g (yield of 64% on the basis of phthalic anhydride) of phthaloyl dichloride having a b p. 120 to 122° C./4-5 ton were obtained (value described in literature b p 131-133° C./9-10 mmHg. Organic Synthesis Coll. Von page 528). A GC analysis of the product confirmed that a residual rate of phthalic anhydride is 0.84% and a purity of the target compound is 99.1%.

Example 2-2

A mixture of 73.8 g (0.50 moles) of phthalic anhydride, 177 g (0.90 moles) of (trichloromethyl)benzene and 0.41 g (1% by mole with respect to phthalic anhydride) of zinc oxide was stirred at 155° C. for 13 hours. By GC analysis of the reaction mixture, it was found that 1.4% of phthalic anhydride remained. Accordingly, 46 g of (trichloromethyl)benzene was added and the resultant reaction liquid was heated to 195° C. and stirred for 4 hours. GC analysis confirmed that a residual rate of phthalic anhydride was reduced to 0.35% and 99.3% of phthaloyl dichloride has been produced.

Example 2-3

A mixture of 35 g (0.19 moles) of 4-chlorophthalic anhydride, 57.5 g (0.25 moles) of 1-chloro-4-(trichloromethyl) benzene and 0.15 g (1% by mole with respect to 4-chlorophthalic anhydride) of zinc oxide was stirred at 155° C. for 4 hours, at 170° C. for 28 hours, and at 200° C. further for 6 hours. GC analysis confirmed that a residual rate of 4-chlorophthalic anhydride was reduced to 0.7% and 99.0% of 4-chloro phthaloyl dichloride has been produced. A structure of the reaction product was confirmed by GC-MS (GC-MS results: m/z=201($M^+$-35, relative intensity 100%), 203 (relative intensity 64%)).

Example 2-4

411.8 g (1.79 moles) of 1-chloro-4-(trichloromethyl)benzene and 1.112 g (0.0136 moles) of zinc oxide were mixed and stirred at 160° C. for 2 hours. GC analysis confirmed that 0.32% of 4-chlorobenzoyl chloride has been produced. If zinc chloride is produced in the same amount as the above, it is estimated by calculation that 0.0057 moles of high-activity zinc chloride is present. To this, 200 g (1.35 moles) of phthalic anhydride was added and stirred at 160° C. for 27 hours. By GC analysis, it was found that 2.5% of phthalic anhydride remained. Accordingly, temperature was increased to 200° C. and further stirring was carried out for 6 hours. As a result, a residual rate of phthalic anhydride was reduced to 0.53%.

Comparative Example 2-1

A mixture of 148 g (1.0 mole) of phthalic anhydride, 299 g (1.3 moles) of 1-chloro-4-(trichloromethyl)benzene and 1.37 g (0.01 moles) of zinc chloride was stirred at 200° C. for 12 hours. By GC analysis of the reaction mixture, it was found that 3.7% of phthalic anhydride remained. Then, a reaction was continued and, 14 hours later and 16 hours later, GC analysis was conducted. Residual rates of phthalic anhydride were 4.15% and 4.10%, which rates were not reduced any more.

Comparative Example 2-2

A mixture of 150 g (1.013 rages) of phthalic anhydride, 228 g (1.165 moles) of (trichloromethyl)benzene and 0.84 g (0.006 moles) of zinc chloride was stirred at 200° C. for 20 hours. GC analysis of the reaction mixture confirmed that 2.9% of phthalic anhydride remains and 94.5% of phthaloyl dichloride has been produced.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. A method of producing a phthaloyl dichloride compound, the method comprising:
   providing a compound represented by the following formula (1) and a compound represented by the following formula (2); and
   bringing the compound represented by the following formula (1) and the compound represented by the following formula (2) into reaction, so as to form a compound represented by the following formula (3), in the presence of at least one catalyst selected from the group consisting of zirconium tetrachloride, dichlorooxo zirconium, zirconium hydroxide and hafnium tetrachloride;

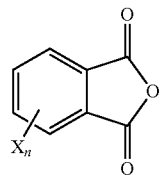
Formula (1)

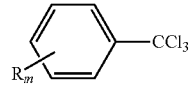
Formula (2)

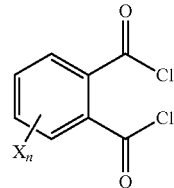
Formula (3)

wherein, in formulae, X represents a halogen atom, a nitro group, a methyl group, or a methoxy group; when the X is plural, Xs may be the same or different from each other; n represents an integer of from 0 to 2; R represents a halogen atom, a chlorocarbonyl group, an alkyl group having 1 to 3 carbon atoms, or a halogen-substituted alkyl group having 1 to 3 carbon atoms; when the R is plural, Rs may be the same or different from each other; and m represents an integer of from 0 to 2.

2. The method of producing a phthaloyl dichloride compound according to claim 1, wherein the compound represented by formula (1) is phthalic anhydride.

3. The method of producing a phthaloyl dichloride compound according to claim 1, wherein the compound represented by formula (1) is 3-chlorophthalic anhydride or 4-chlorophthalic anhydride.

4. The method of producing a phthaloyl dichloride compound according to claim 1, wherein the compound represented by formula (2) is 1-chloro-4-(trichloromethyl)benzene.

* * * * *